United States Patent [19]

Trispel et al.

[11] Patent Number: 4,550,990

[45] Date of Patent: Nov. 5, 1985

[54] ARRANGEMENT FOR THE CARRYING OUT OF EYE EXAMINATION

[75] Inventors: Stephan Trispel; Günter Rau, both of Aachen, Fed. Rep. of Germany

[73] Assignee: Forschungsgesellschaft für Biomedizinische Technik e.V., Fed. Rep. of Germany

[21] Appl. No.: 401,255

[22] Filed: Jul. 23, 1982

[30] Foreign Application Priority Data

Aug. 25, 1981 [DE] Fed. Rep. of Germany ....... 3133608

[51] Int. Cl.$^4$ .............................................. A61B 3/02
[52] U.S. Cl. ................................... 351/243; 351/222; 351/244
[58] Field of Search ............... 351/222, 243, 244, 246; 350/331 R

[56] References Cited

U.S. PATENT DOCUMENTS

| 3,684,355 | 8/1972 | Molner | 351/243 |
| 3,883,234 | 5/1975 | Lynn et al. | 351/243 X |
| 4,212,520 | 7/1980 | Klimsa | 351/243 |
| 4,274,713 | 6/1981 | Krueger | 350/331 R X |

FOREIGN PATENT DOCUMENTS 2528885 4/1977 Fed. Rep. of Germany .

Primary Examiner—Rodney B. Bovernick

Attorney, Agent, or Firm—Ostrolenk, Faber, Gerb & Soffen

[57] ABSTRACT

The invention refers to an arrangement for the carrying out of eye examinations by means of an optotype mask which is illuminated from behind. It consists therein that the optotype mask is arranged in front of the picture screen of a video tube which serves as source of illumination and that means are provided by which the picture-screen presentation can be controlled with respect to brightness, color, contrast, partial or full surface illumination and blending-in of additional static or moving structures in order to carry out different eye tests. In this connection the optotype masks may be exchangeable or be moved over the picture-screen surface by a mechanical drive between different eye tests. Furthermore, the optotype mask may consist of flexible material which may be moved past the surface of the picture screen between different eye tests. Furthermore, means are provided by which both the exchange of the optotype mask and the control of the picture-screen display can be programmed for automating the eye tests. Instead of the video tube and optotype mask there can also be provided a double arrangement consisting of the optotype mask and a flat display which—self-illuminating or reflective—serves as source of illumination or a triple arrangement consisting of the optotype mask and a flat display which serves by transmission as light-valve plane for a static source of illumination arranged behind it.

9 Claims, 12 Drawing Figures

ARRANGEMENT FOR THE CARRYING OUT OF EYE EXAMINATION

BACKGROUND OF THE INVENTION

The invention relates to an arrangement for the carrying out of examinations by means of an optotype mask illuminated from the rear.

The testing of eyesight is becoming increasingly important. The large percentage of people who are not aware of their poor sight is well known. The effects thereof are various and extend from reduced safety in traffic to overstress when working at a video screen. The detection of impairment in sight is particularly important for children of school and primary school age. Here mass examinations can provide help.

Mass examinations are very expensive as long as a highly qualified examiner (a doctor) must carry out the entire examination himself. Accordingly, great efforts are being made to develop these examinations as partially or fully automated eye tests. Certain viewing functions can actually be carried out automatically without the presence of an examiner. The test can adaptatively adapt itself to the decision response (answers) of the test subject, and in this connection the equipment can be developed in such a manner that the course of the testing is determined automatically by a predetermined program. The eye-test examining device, on the other hand, should also make it possible for the eyesight tests to be effected in traditional manner by the Examiner (doctor).

THE PRIOR ART

Traditional arrangements operate either in reflected light with tables on which the optotypes or colored fields are printed or else they employ projection systems by means of which the test characters are projected either onto a screen or into a viewing apparatus. In viewing apparatus, optotype masks are illuminated from the rear by a lamp. This principle exists also as light-box arrangements in connection with presentations at different viewing distances. The difficulty in using these arrangements for an automated test is that the stimulus material offered must be continuously changed in accordance with the previously unknown response of the test subject. The electronic video screen on which optotypes can be shown synthetically offers a solution for this (see U.S. patent application Ser. No. 945,943 of Sept. 26, 1978 now U.S. Pat. No. 4,239,351). However, the resolution of a video screen is limited. It can, for instance, be shown that its resolution for optotypes is not sufficient in a near-vision test; the optotypes are not developed with sufficiently fine structure on the screen.

OBJECT OF THE INVENTION

The object of the invention is to provide an arrangement for the carrying out of eye examinations which permits, at little expense, better and more extensive possibilities for the testing of eyesight than the known arrangements and which combines the advantages of an ordinary illuminated optotype mask with the advantages of a display device, particularly a video tube, as support for special characters so as to obtain new test possibilities.

Furthermore, the invention is directed at providing an arrangement for the carrying out of eye examinations which makes it possible to carry out automatic eye tests without requiring the presence of a skilled examiner (doctor).

Furthermore, the invention is directed at making available an arrangement for the carrying out of eye examinations in which the eye test can adapt itself adaptatively to the decision response (answers) of the test subject, the arrangement being so developed that the course of the test is automatically determined by a predetermined program; the arrangement, on the other hand, should also make it possible for the eye tests to be carried out in traditional manner by the examiner (doctor).

Finally, by the invention there is to be made available an arrangement for the carrying out of eye examinations in which the modern techniques of flat displays are used and thus a substantial improvement is obtained with respect to compactness of apparatus, price-performance ratio and quality of picture.

SUMMARY OF THE INVENTION

This is achieved in accordance with the invention in the manner that the optotype mask is arranged in front of a display device the brightness, color, contrast and partial or full surface illumination of which can be controlled in order to carry out different eye tests and on which additional static or moving structures can be presented and blended into the field of view of the optotype mask for the carrying out of the eye tests; and that a display control device for controlling the brightness, color, contrast and partial or full surface illumination and the generation of additional static or moved structures is connected to the display device.

In particular the arrangement can be developed in the manner that the display device is the picture screen of a video tube or that the display device is a self-illuminating or reflective flat display device, in particular a plasma, pyrope, electroluminescence or light-dispersing liquid crystal display device.

Another possibility resides in the display device being a flat display device which comprises a static source of light, in particular an incandescent-filament or gas-discharge lamp, and a flat two-dimensional light-valve device, particularly a transmissive liquid-crystal device or a ferroceramic display device which form a selective illuminating device for the optotype.

The expression "flat two-dimensional light-valve device" means a light-valve plane, the expression "light valve" designating the property of this light-wave plane as a result of suitable control to be selectively light-transmitting or impervious. In this connection static and/or dynamic geometrical "valve structures" can be used which supplement the presentation function of the optotype mask arranged in front thereof. Thus in accordance with the invention one obtains a triple arrangement consisting of optotype mask, light valve plane and static illumination source. In this way, in the same manner as when using a self-illuminating or reflective flat display device an improvement with respect to compactness of the apparatus, price-performance ratio and quality of picture is obtained as compared with the use of a video tube as display device.

The arrangement in accordance with the invention is preferably developed in the manner that a holding and/or positioning device for the optotype mask is provided by which the latter can be rapidly replaced between vision tests either manually or mechanically and/or the position of the display device can be varied with respect to the display surface by a mechanical drive. In this connection the development may in particular be such that the optotype mask consists of flexible and particularly rollable mask material and can be moved in over the display surface by means of the holding and/or positioning device, the holding and/or positioning device preferably comprising a take-off roller for the unwinding of the optotype mask and a take-up roller for the winding up of the optotype mask as well as possibly guide rollers for guiding the optotype mask over the display surface. In all of these cases it is preferable that an exchange and/or positioning device be provided for the controllable actuating of the holding and/or positioning device.

In particular the arrangement can be developed in such a manner that a programmable control device, in particular one or more microprocessors, is provided for the programmable operation of the display control device and of the exchange and/or positioning control device by which both the exchanging and/or positioning of the optotype mask as well as the control of the display surface and/or the display itself can be programmed for partial or complete automating of the eye tests. For the automating of the tests, therefore, not only is the transillumination of the optotype mask defined by the display device as source of light utilized but an active picture plane for selection from a plurality of characters or electronic structural images can be introduced which serves to guide the observer's attention or for comments.

Finally, it is possible for a display surface luminance control device to be provided in order to control or regulate the luminance of the display surface as a function of a predetermined display surface luminance and/or the intensity of the incident ambient light, a programmable control device being preferably provided, in particular a microprocessor, for the programmable operation of the display-surface luminance test control device.

In this way the background luminance level as a whole can be maintained constant by brightness control as a result of which the state of adaptation of the test subject remains constant.

BRIEF DESCRIPTION OF THE DRAWING

The foregoing as well as other purposes, advantages and features of the invention will be described in further detail below on basis of a few particularly preferred embodiments of the invention with reference to FIGS. 1 to 12 of the drawing in which.

DETAILED DESCRIPTION OF THE INVENTION: THE PREFERRED EMBODIMENTS

On basis of FIGS. 1 to 6 there will first of all be explained various embodiments of the display device with optotype mask arranged in front of it.

In FIGS. 1 to 4, the display device is a video monitor 1 whose display surface 2 is the picture screen of a video tube. As seen by the observer, in front of the display surface 2 there is an optotype mask 3 which consists essentially of a completely or partially transparent base 4 on which optotypes 5 are provided, for instance by printing.

Figure 1:
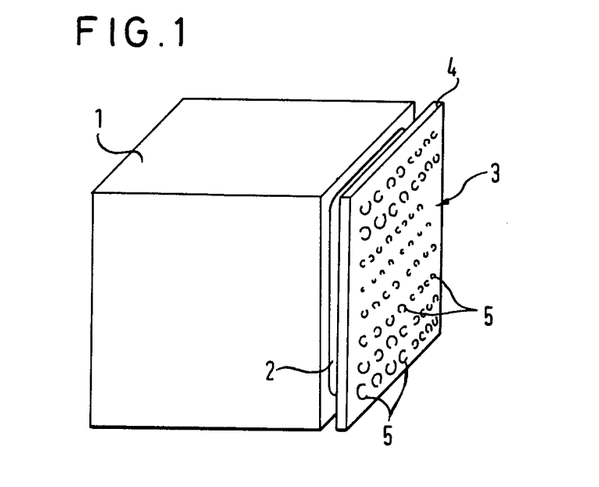
FIG. 1 shows a first preferred embodiment of an arrangement for the carrying out of eye tests in accordance with the invention using a television monitor as display device with an optotype mask arranged in front of it.
Figure 2:
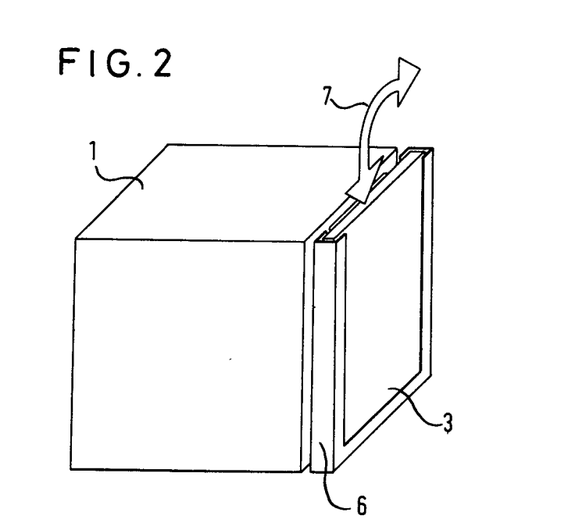
FIG. 2 shows an arrangement similar to FIG. 1 but in which the optotype mask is arranged in replaceable manner in a holding device developed as a frame.

While in the embodiment shown in FIG. 1 the optotype mask 3 is simply arranged in front of the display surface 2 or applied by adherence to the display surface 2 from which it can possibly be removed again, the sheet or plate-shaped optotype mask 3 is inserted in the arrangement shown in FIG. 2, into a frame 6 which is located in front of the display surface 2. The frame 6 is open on one side, in the present case on top, so that the optotype mask 3 can be easily pulled out and replaced by a different optotype mask, as indicated by the double-ended arrow 7. The frame 6 therefore forms a holding device for the manual changing of the optotype support 3.

The optotypes 5 in the present embodiment are Landolt rings in all sizes to be tested, which may be applied also photographically to the base 4.

Figure 3:
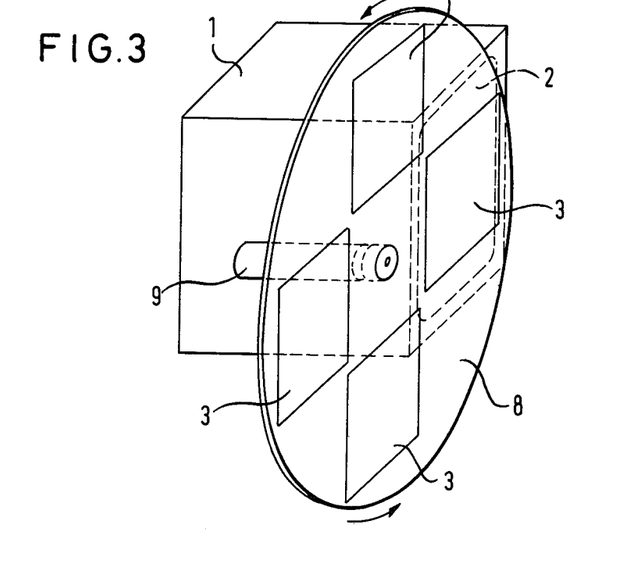
FIG. 3 shows a second preferred arrangement in accordance with the invention in which the optotype masks are arranged on four fields of a rotatable disk in front of a television monitor as display device.

In the embodiment shown in FIG. 3, a rotary disk 8 which is rotatable about an axis 9 as indicated by the two arrows is provided as holding device for a plurality of optotype masks 3, so that any one of the four optotype masks 3 desired can be turned in front of the display surface 2.

Figure 4:
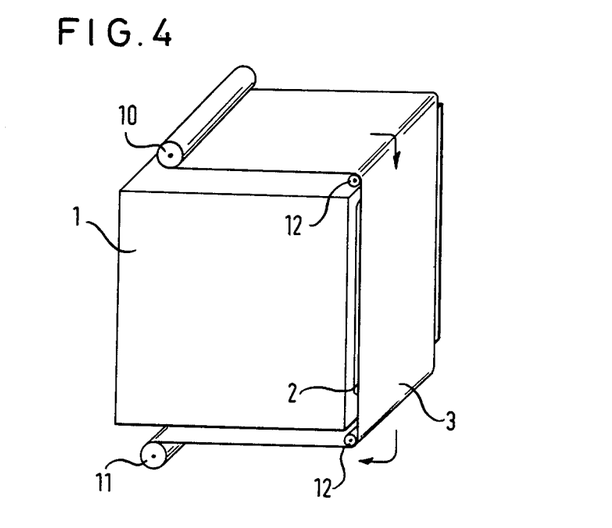
FIG. 4 shows a third preferred embodiment of the invention in which the optotype mask is a windable foil which can be wound up in front of the picture screen of the television monitor which forms the display device.

In the arrangement shown in FIG. 4, the optotype support 3 consists of a flexible base as mask material for the optotypes and a take-off roller 10 for the unwinding of the optotype mask 3 and a take-up roll 11 for the winding thereof are provided as holding and/or positioning device, guide rollers 12 being furthermore provided in the vicinity of the upper and lower edges of the display surface 2 in order to guide the optotype mask 3 into a predetermined position over the display surface 2. As indicated by the two arrows in FIG. 4 it is possible in this way for the optotypes present on the optotype support 3 to be moved over the display surface 2 and thus also positioned in vertical direction of the display surface 2.

The changing of the optotype mask 3 in FIG. 3 or the positioning of the different optotype fields of the optotype mask 3 in FIG. 4 can be effected manually or by microprocessor control in such a manner that in each case one optotype field is positioned precisely in front of the display surface 2.

Figure 5:
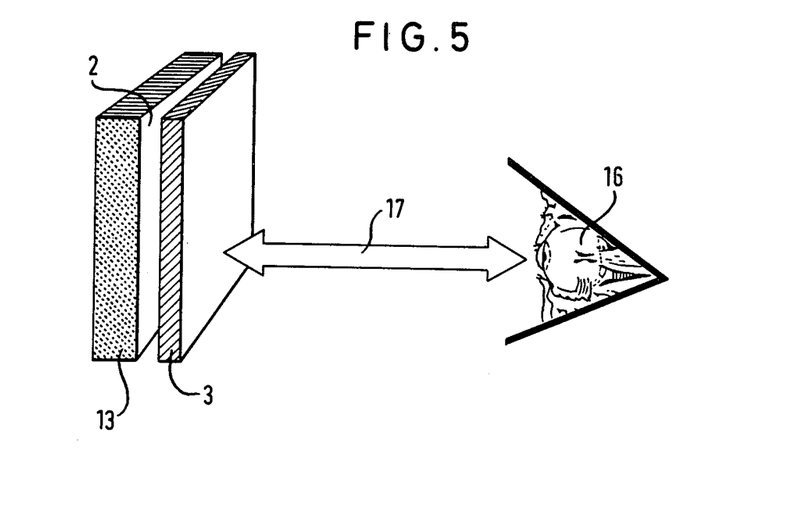
FIG. 5 is a flat, active display device having an optotype mask arranged in front of it.
Figure 6:
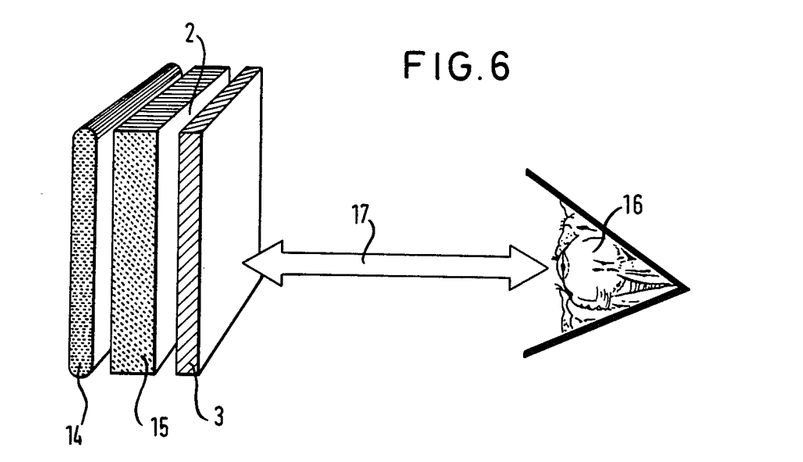
FIG. 6 is a display device consisting of a passive light source and a two-dimensional flat light valve arrangement with optotype mask arranged in front thereof.

FIGS. 5 and 6 show two further display devices with associated optotype mask 3, which display devices can be used in all embodiments of the invention described instead of the video monitor 1, the optotype mask 3 being developed in one of the different types and being held and possibly positionable in the manner which has been described with reference to FIGS. 1 to 4.

In the embodiment of FIG. 5, the display device consists of a flat device display 13 which is either self-illuminating or reflective; in the former case it may be a plasma display, a pyrope display, an electroluminescence display, etc. while in the latter case the display may consist, for instance, of light-dispersing liquid crystals.

In the embodiment shown in FIG. 6, the display device comprises a flat passive or static light source 14 such as, for instance, an incandescent filament or gas-discharge lamp and a flat two dimensional light valve device 15 arranged in front of it as seen by the observer. The light-valve device may, for instance, be a transmitting liquid-crystal device or a ferroceramic display device.

Figure 7:
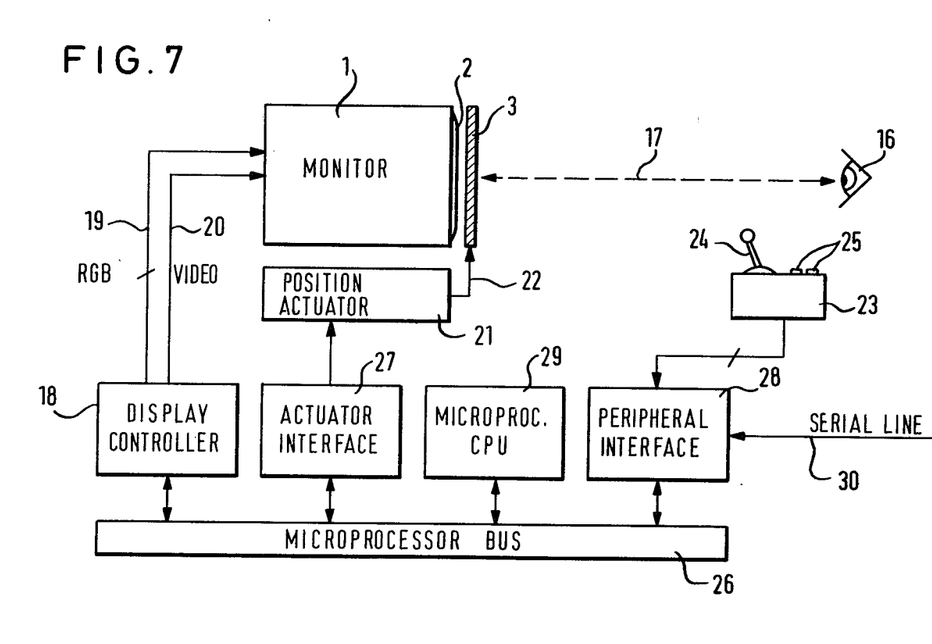
FIG. 7 shows another preferred arrangement in accordance with the invention having a control device for the carrying out of eye tests which comprises in particular a display control device, a position control device for the optotype mask and a programmable microprocessor.

The display devices, namely the video monitor 1 or the active display 13 or the combination consisting of the passive light source 14 and the light valve device 15 can be so controlled by suitable means that the different parameters such as brightness, color, contrast, partial or full surface control and blending-in of static or dynamic structures can be manipulated on the display surface 2 in the desired manner as required for the specific eye test for the eye 16 of the observer (the direction of view of the observer and the rays entering into the eye 16 of the observer from the display device and the optotype mask are indicated by a double-ended arrow 17 in FIGS. 5, 6 and 7). It may be pointed out that the control of the aforementioned parameters in FIG. 5 is effected by suitable control of the active programmable display 13 while in contradistinction hereto this control is effected in FIG. 16 substantially by control of the light valve device 15 in that given regions of this light-valve device are made light-transmitting while other regions are made light-opaque, the light transmittance being also possibly controlled by suitable screening in the light-valve device and/or the illuminance and/or color of the source of light 14 being controlled.

Reference may now be had to FIG. 7 in which a complete arrangement for the automatic carrying out of eye tests is shown. This arrangement comprises a display device, for instance a video monitor 1, in front of whose display surface 2 an optotype mask 3 is arranged. The optotype mask 3 and the holding and positioning device for same (not shown in FIG. 7) can be developed, for instance, in the manner shown in FIG. 4. To the video monitor 1 there is connected a display controller 18 by means of which the color of the display surface 2 is controlled via a line 19 and the control of the brightness, contrast, partial or full surface illumination and blending in of static or dynamic structures can be effected via a line 20. For the exchanging and positioning of the optotype mask 3 an exchanging and/or positioning control and actuating device 21 is connected to the holding and positioning device for the optotype mask 3, as indicated by the arrow 22. Furthermore, an operating device 23 is provided by means of which the user can seek or mark the corresponding optotypes and/or enter his answers as to the recognition of the optotypes. This operating device has an operating element 24 as well as possibly several switches 25.

The display controller 18 is connected directly by a microprocessor bus 26 to a central unit or microprocessor 29, the exchange and/or position controller and actuator 21 being connected thereto via an internal interface 27 and the operating device 23 via a peripheral interface 28, a serial line 30 being connected to the peripheral interface for the connecting of other apparatus.

The microprocessor 29 serves as central unit carries out in particular the following functions:

(a) Symbol representations on the display surface 2. Such symbols may, for instance, be a luminous field 31 (see FIG. 8) for the isolated or emphasized illumination of an optotype 5 which is to be recognized at the time or a frame marking 32 for characterizing an optotype 5 which is to be recognized (see FIG. 9).

(b) Movement of the optotype mask 3.

(c) Detection of control or response inputs of the person whose sight is to be tested, which are entered via the operating device 23.

(d) Communication with other apparatus via the serial interface 28 and the serial line 30.

(e) Selection of in each case the next optotype 5 in the automatic test with preferably adaptive test strategy and other calculations and storings.

Therefore, with the microprocessor 29, the entire arrangement can be operated in programmable fashion so that thus partially or completely automated eye tests can be carried out, the exchange of the optotypes and the control of the display being effected in programmed fashion via the microprocessor.

Figure 10:
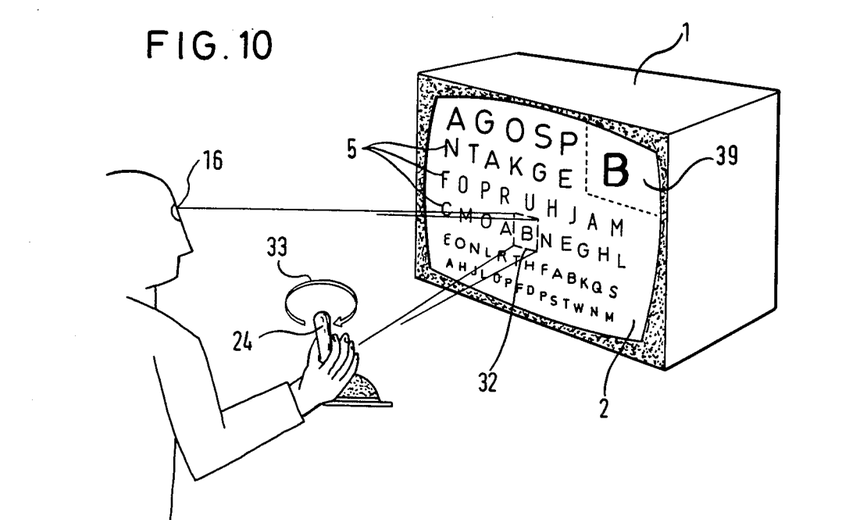
FIG. 10 is a view of a letter or number eye test using one embodiment of an arrangement in accordance with the invention.

FIG. 10 shows the carrying out of an eye test with letters as optotypes 5, the ring-shaped arrow 33 indicating the possibility of movement of the operating element 24. This eye test is described in further detail below under the heading "Examples."

Figure 11:
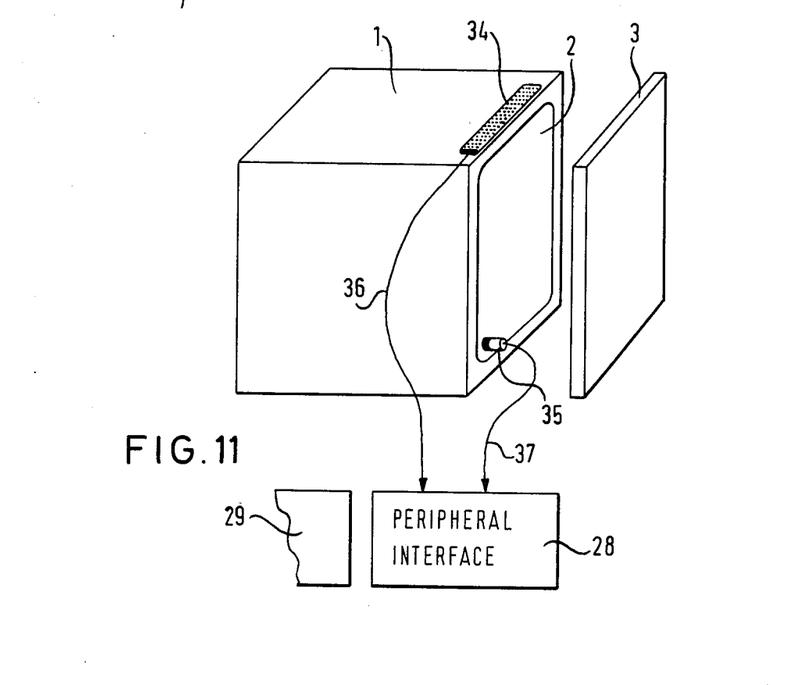
FIG. 11 is an arrangement which corresponds to FIG. 1 in which, however, in addition the illuminance of the ambient light and the luminance on the display surface located in front of the picture screen of a video tube are measured.
Figure 12:
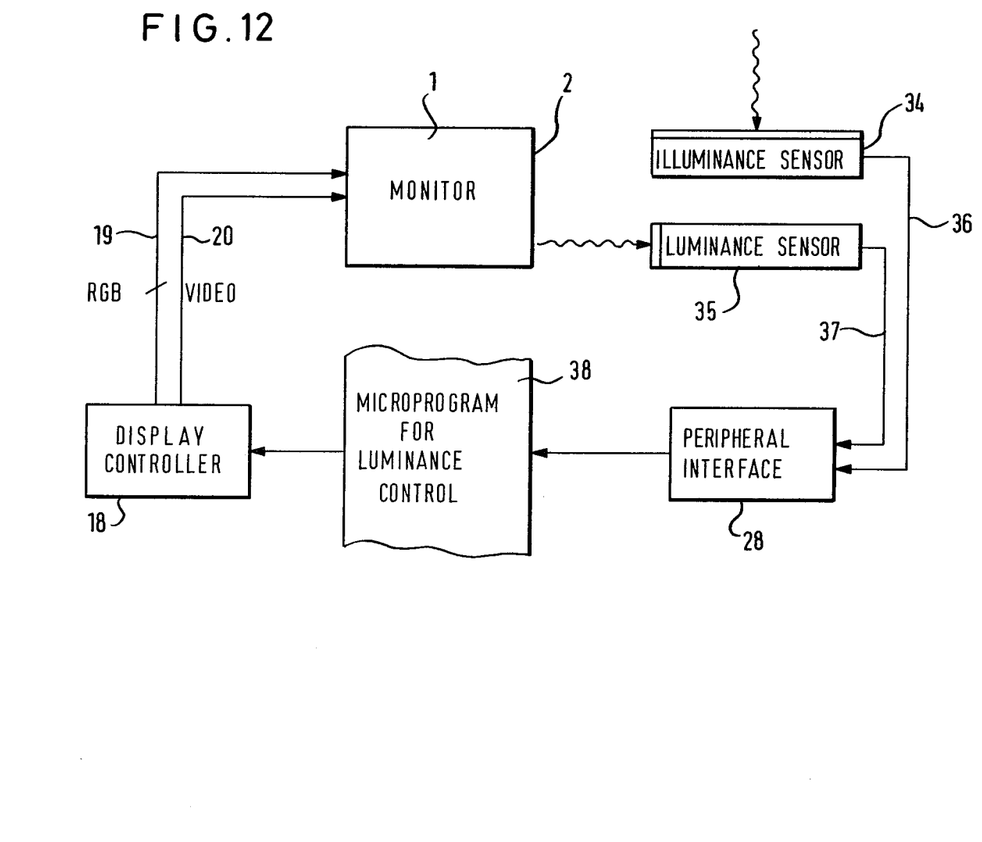
FIG. 12 is a block diagram of a preferred arrangement in accordance with the invention by which it is possible, with the use of the arrangement shown in FIG. 11, to control the luminance of the display surface as a function of the measured illuminance of the ambient light for a predetermined contrast of the optotypes in front of the display screens.

Finally, as shown in FIGS. 11 and 12, a display luminance control device for controlling or regulating the luminance of the display surface 2 as a function of a predetermined display surface luminance and/or the intensity of the incident ambient light can be provided. This display surface luminance controller comprises an illuminance sensor 34 by which the illuminance produced by the incident ambient light is measured and a luminance sensor 35 by which the luminance on the display surface 2 is measured. The illuminance sensor 34 and the luminance sensor 35 are connected via corresponding wires 36 and 37 to the peripheral interface 28. These sensors may, for instance, be photodetectors. In order to determine the illuminance and the luminance the ordinary electronic devices can be provided, in particular an analog to digital converter, etc.

As shown in FIG. 12, the actual control of the display surface luminance takes place via the microprocessor 29 whose microprogramming part 38 for the controlling or regulating of the luminance as indicated in FIG. 12; the microprocessor 29 therefore contains the control algorithm on basis of which the command for adjusting the illuminance of the display surface 2 is given via the display controller 18, which may, for instance, be a raster display controller. The luminance of the display surface 2 is controlled or regulated for a given contrast of the overall arrangement consisting of display surface 2 and optotype mask 3 arranged in front thereof.

It may be pointed out that in the different figures of the drawings identical or similar parts have been provided with the same reference numbers.

EXAMPLES

(1) Automated Eye Test

The optotype mask may be provided simultaneously with a plurality of optotypes. As example, in the case of a vision test (near vision, viewing distance 30 to 80 cm) this may be 64 optotypes (Landolt rings) for testing the visual acuity values 0.1–3.2 (according to DIN 58220). The optotypes can be emphasized or presented by controlling the picture screen (marking).

Figure 8:
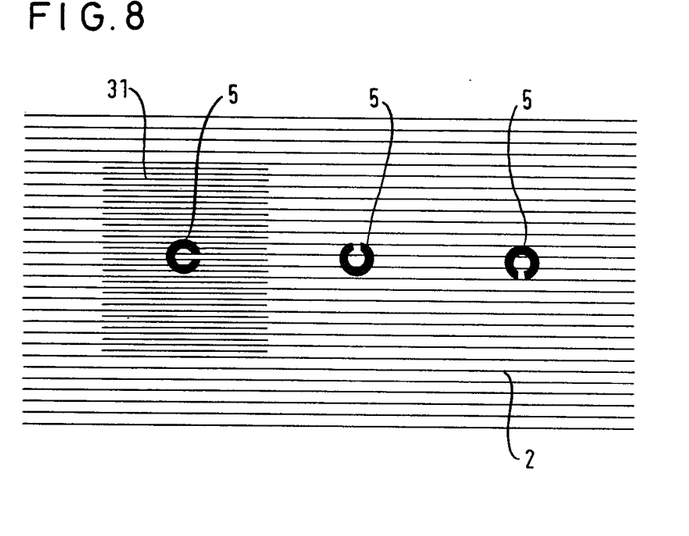
FIGS. 8 and 9 are views of an optotype mask behind which there is a display device by which the optotype which is to be noted in each case is marked by a special optotype field or an optotype frame.

(a) Isolated transillumination of an optotype field by luminous field 31 with a defined luminance of between 0 and max. 1500 $cd/m^2$, in accordance with FIG. 8.

The background luminance can be kept low (for instance 50 $cd/m^2$). Thus the optotype to which the test subject is to react is defined by marking. The values of between 200 and 500 $cd/m^2$ described in accordance with DIN 58220 can be set within the operating range.

Figure 9:
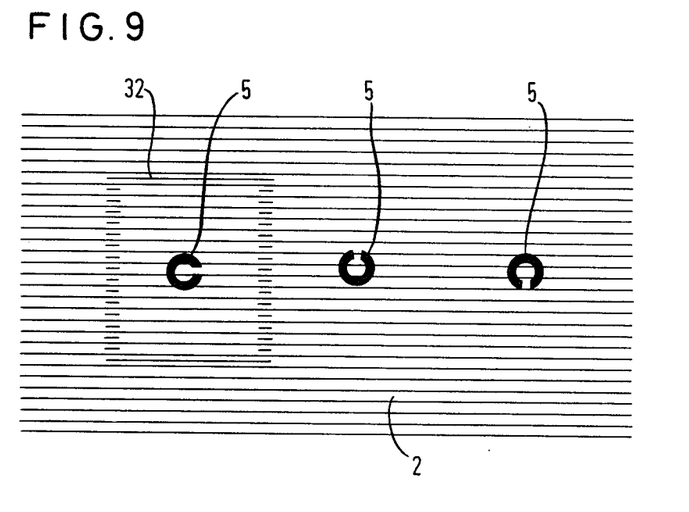

(b) The transillumination of the entire optotype field simultaneously with defined luminance (DIN 58200; 200–500 $cd/m^2$) and the framing of the optotype field by a frame marking 32, particularly a luminous frame of different shape, color or luminance which is produced as display or television picture, as shown in FIG. 9. With respect to the marking it may be stated that it can take place completely automatically or semi-automatically. Both marking possibilities can also be used for other optotypes (standardized optotypes such as, for instance, the Snellen E).

The principle can also be applied to rows of letters or numbers. In this connection at the present time due to reasons of test techniques only semi-automatic operation is possible, i.e. an examiner (doctor) marks the individual rows or optotypes. With improved automatic presentation strategies, however, automization is possible here also.

(2) Automated Letter or Number Test

A combination of optotype field with display or television picture opens up expanded automated test possibilities, as explained below, using as example a letter or number test with reference to FIG. 10:

At a suitable point 39 (upper right corner in the Example) an optotype in shown black on white in large size as display or television picture. This picture can be rapidly changed by a display or television generator. The test subject using an operating element 24 (for instance a joy stick) by which a frame 32 which is blended into the display or television picture can be moved in x or y direction, seeks the optotype which he is asked to recognize in the fixed optotype arrangement. Alternatively, or in addition, an optotype mask plate may also be moved by the joy stick signal in front of the display surface. If the marking 32 is moved only in a line then the rate of hits is determined by the predetermination (line) of the optotypes to be sought which are then located within the line in a test region.

(3) Further Test Possibilities

For various tests standards have in part been established, as for instance in the vision test.

(a) Near Vision

Viewing distance 30–50 cm; here the quality of the optotypes can be obtained only with the optotype mask.

(b) Far Vision in Viewer

In a viewer the configuration of optotype mask combined with image screen is unchanged but the stimulus is, by an optical system with respect to the ray path, offered at a distance seemingly at an infinite distance.

(c) Viewing Device: Scotopic Vision Test and Dazzle Test

The far vision in accordance with (b) can be expanded, by controlled quasi-infinitely variable variation of the monitor luminance to a Scotopic vision test. A dazzle test can also be included by carrying out the visual acuity test with parafoveal dazzle by simulated automobile headlights or other sources of disturbing light of different size and luminance on the monitor. All of these displays are produced electronically and offered in defined fashion under computer control.

(d) Far Vision in Distance Presentation

Far vision is standardized, at least for medical investigations. The standardization relates to the optotypes (isolated optotypes) and to the viewing distance. With a large viewing distance the resolution of the television screen display is adequate. The optotypes (for instance Landolt rings, E hooks) are produced on the electronic picture screen namely without an optotype mask in front. The selection and size are again determined automatically by the microcomputer, the response of the test subject being taken into consideration in accordance with a strategy for the selection of in each case the next optotype offered.

(4) Evaluation

After each test, the acuity of vision of the test subject can be shown optically on the test apparatus itself. Here optotypes can be marked differently depending upon whether they were recognized definitely, not definitely or not at all. The characterizing of the individual optotypes is effected, for instance, by framing or by backgrounds of areas of different intensity or color.

In conclusion, the manner of operation of the arrangement in accordance with the invention will be explained on basis of an eye-test program which has already been carried out and tested:

On the optotype mask 3 there are 64 optotypes 5 for determining (near) vision (visual acuity), namely Landolt rings (the slot opening can be located at the top, bottom, left or right in the ring). The display surface 2, for instance the picture screen of a video tube behind the diffusely transparent optotype plate 3 is adjusted to a certain basic brightness over its entire surface. At the start of the test a microcomputer 26 via the picture processor 18 causes the presentation of a bright area 31 (round or square or else a different shape) on the display surface 2 behind one of the optotypes 5. In this way the attention of the test subject is directed to this optotype. This optotype is not visible with a given ambient luminance and with a given contrast and the test subject reacts by entering the observed position of the slot (top, bottom, left, right) either by correspondingly deflecting joy stick or by actuating a key 25 which corresponds to the position of the slot. The optotype background illumination then goes out and the microcomputer 29, in accordance with the logical course of the program, causes the illumination of the next optotype 5. This process is repeated until the computer-controlled termination of the test in accordance with the program established.

From the test examples given it can be seen that as a result of the arrangement in accordance with the invention substantially more test possibilities and test runs are possible than in the case of the known arrangements and—what is particularly important—all possible test programs can be automatically set by this arrangement.

We claim:

1. An arrangement for the carrying out of eye examinations by means of a transparent optotype mask carrying a variety of optotypes illuminated from the rear, characterized by the fact that the optotype mask is arranged in front of a display device whose brightness, color, contrast and partial or complete surface illumination can be controlled for the carrying out of different eye tests, and on which additional static or moving structures can be generated and shown in the field of view of the optotype mask for the carrying out of the eye tests; and that a display control device for the controlling of the brightness, color, contrast or the partial or complete surface illumination and the generation of additional static or moving structures is connected to the display device; and a programmable control device, particularly one or more microprocessors for the programmable operation of the display control device and of the exchange and/or position control device, by which, for the partial or complete automating of the eye test, both the changing and/or positioning of the optotype masks and the control of the display surface and/or of the display presentation can be programmed.

2. An arrangement according to claim 1, characterized by the fact that the display device is the picture screen of a video tube.

3. An arrangement according to claim 1, characterized by the fact that the display device is a self-illuminating flat display device such as a plasma, pyrope or electroluminescence display or a reflective display device such as a light-dispersing liquid-crystal display device.

4. An arrangement according to claim 1, characterized by the fact that the display device is a flat display device which comprises a static source of light, particularly an incandescent-filament or gas-discharge lamp, and a flat two-dimensional light valve device illuminated by same, particularly a transmissive liquid-crystal device or a ferroceramic display device which form a selective illuminating device positioned behind the optotype mask.

5. An arrangement according to claim 1, characterized by the fact that a holding and/or positioning device for the optotype mask is provided by which the latter can be exchanged manually or mechanically and/or varied in its position by means of a mechanical drive with respect to the display surface of the display device between different eye tests.

6. An arrangement according to claim 5, characterized by the fact that the optotype mask consists of flexible and particularly of rollable support material and can be moved by means of the holding and/or positioning device into a predetermined position in front of the display surface, the holding and/or positioning device preferably comprising a take-off roll for the unwinding of the optotype mask and a take-up roll for the winding-up of the optotype mask as well as, possibly, guide rolls for guiding to optotype mask over the display surface.

7. An arrangement according to claim 5, characterized by the fact that an exchange and/or position control device is provided for the controllable actuation of the holding and/or positioning device.

8. An arrangement according to claim 1, characterized by the fact that a display-surface luminance control device is provided for controlling or regulating the luminance of the display surface as a function of the predetermined display-surface luminance and/or of the intensity of the incident ambient light.

9. An arrangement according to claim 8, characterized by the fact that a programmable control device, particularly a microprocessor, is provided for the programmable operation of the display-surface luminance control device.

* * * * *